United States Patent
Bae et al.

(10) Patent No.: US 12,102,483 B2
(45) Date of Patent: Oct. 1, 2024

(54) ULTRASONIC SHEARWAVE IMAGING WITH PATIENT-ADAPTIVE SHEARWAVE GENERATION

(71) Applicant: KONINKLIJKE PHILIPS N.V., Eindhoven (NL)

(72) Inventors: Unmin Bae, Kenmore, WA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/886,153

(22) Filed: Aug. 11, 2022

(65) Prior Publication Data

US 2022/0386996 A1 Dec. 8, 2022

Related U.S. Application Data

(62) Division of application No. 16/755,380, filed as application No. PCT/EP2018/076042 on Sep. 26, 2018, now Pat. No. 11,446,007.

(Continued)

(51) Int. Cl.
*A61B 8/08* (2006.01)
*A61B 8/00* (2006.01)
*A61B 8/06* (2006.01)

(52) U.S. Cl.
CPC ................ *A61B 8/485* (2013.01); *A61B 8/06* (2013.01); *A61B 8/085* (2013.01); *A61B 8/461* (2013.01);

(Continued)

(58) Field of Classification Search
CPC ........... A61B 8/485; A61B 8/06; A61B 8/085; A61B 8/461; A61B 8/488; A61B 8/5223; A61B 8/5246; A61B 8/5276; A61B 8/543; A61B 8/5269; A61B 8/5207; A61B 8/54; A61B 8/585; G01S 7/52095; G01S 15/8915; G01S 7/52022; G01S 7/52042; G01S 15/8979; G16H 50/30
See application file for complete search history.

(56) References Cited

U.S. PATENT DOCUMENTS 4,644,795 A 2/1987 Augustine
5,318,033 A 6/1994 Savord
(Continued)

FOREIGN PATENT DOCUMENTS

EP 2926739 A1 10/2015

OTHER PUBLICATIONS

Berbeco et al, Residual motion of lung tumours in gated radiotherapy with external respiratory surrogates, 2005 Phys. Med. Biol. 50 3655-3667, DOI 10.1088/0031-9155/50/16/001.*

(Continued)

*Primary Examiner* — Bo Joseph Peng

(57) ABSTRACT

An ultrasonic diagnostic imaging system acquires different kinds of pilot images showing different characteristics of a region of a body where shearwave measurements are performed. The pilot images are analyzed by a push pulse locator to adaptively generate push pulses at locations in the body which minimize or avoid shearwave travel through blood vessels, through regions of stiffness inhomogeneities in the body, or at times when shearwaves are adversely affected by tissue motion.

9 Claims, 5 Drawing Sheets

Related U.S. Application Data

(60) Provisional application No. 62/571,456, filed on Oct. 12, 2017.

(52) U.S. Cl.
CPC ............ *A61B 8/488* (2013.01); *A61B 8/5223* (2013.01); *A61B 8/5246* (2013.01)

(56) References Cited

U.S. PATENT DOCUMENTS

| | | | |
|---|---|---|---|
| 5,345,426 A | 9/1994 | Lipschutz | |
| 5,469,851 A | 11/1995 | Lipschutz | |
| 5,810,731 A | 9/1998 | Sarvazyan et al. | |
| 6,494,838 B2 | 12/2002 | Cooley et al. | |
| 6,695,783 B2 | 2/2004 | Henderson et al. | |
| 8,500,639 B2 | 8/2013 | Yao | |
| 8,545,410 B2 | 10/2013 | Simpson et al. | |
| 9,107,564 B2 | 8/2015 | Burcher et al. | |
| 9,468,421 B2 | 10/2016 | Benson et al. | |
| 2011/0063950 A1* | 3/2011 | Greenleaf ........... G01S 7/52038 | 367/87 |
| 2012/0065507 A1* | 3/2012 | Brunke ............... A61B 8/485 | 600/442 |
| 2012/0215101 A1* | 8/2012 | Maleke ............... A61B 5/055 | 600/438 |
| 2013/0123630 A1* | 5/2013 | Freiburger .......... A61B 8/485 | 600/443 |
| 2015/0119710 A1 | 4/2015 | Kawae et al. | |
| 2015/0141821 A1 | 5/2015 | Yoshikawa et al. | |
| 2015/0148674 A1 | 5/2015 | Park et al. | |
| 2015/0272547 A1* | 10/2015 | Freiburger ............ A61B 8/52 | 600/438 |
| 2015/0342566 A1 | 12/2015 | Matsumoto et al. | |
| 2016/0143621 A1 | 5/2016 | Parthasarathy et al. | |
| 2016/0249884 A1 | 9/2016 | Hashimoto et al. | |
| 2016/0345939 A1 | 12/2016 | Toji | |
| 2017/0224304 A1 | 8/2017 | Sonoyama et al. | |

OTHER PUBLICATIONS

International Search Report and Written Opinion for International Application No. PCT/EP2018/076042, filed Sep. 26, 2018, 14 pages.

\* cited by examiner

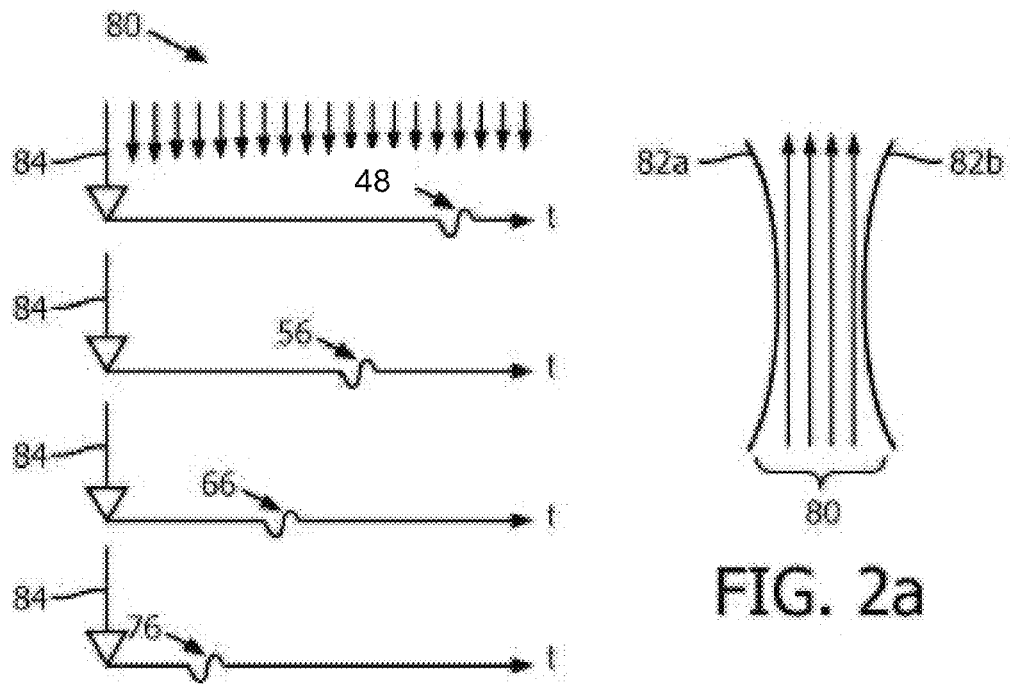
FIG. 2 Amended
FIG. 2a
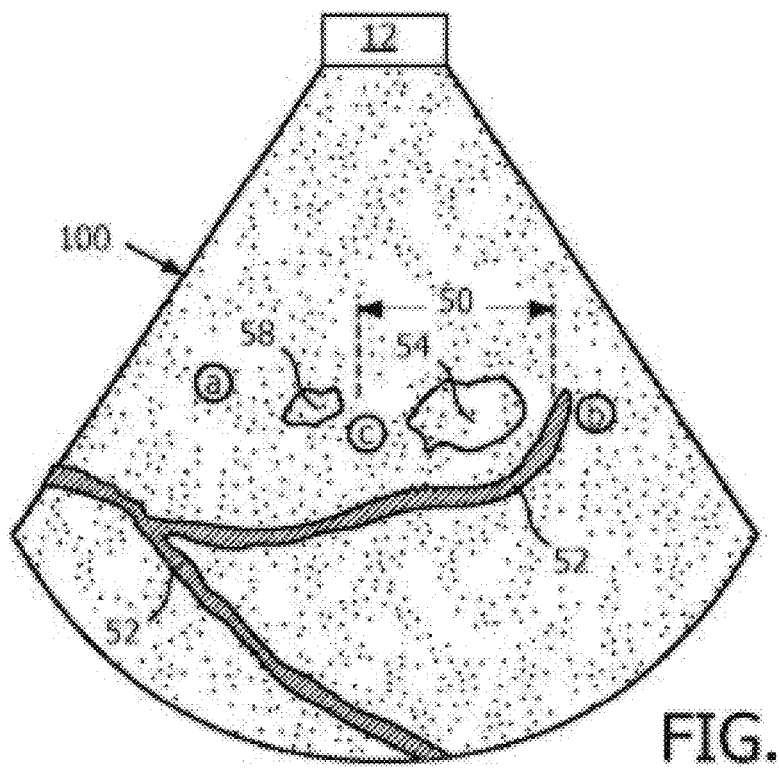
FIG. 3

ULTRASONIC SHEARWAVE IMAGING WITH PATIENT-ADAPTIVE SHEARWAVE GENERATION

The present application is a divisional application of U.S. patent application Ser. No. 16/755,380 filed Apr. 10, 2020, which is the U.S. National Phase application under 35 U.S.C. § 371 of International Application No. PCT/EP2018/076042, filed Sep. 26, 2018, which claims the benefit of U.S. Provisional Application Ser. No. 62/571,456 filed Oct. 12, 2017. These applications are hereby incorporated by reference herein.

This invention relates to medical diagnostic ultrasound systems and, in particular, to ultrasound systems which perform measurements of tissue stiffness or elasticity using shearwaves.

One of the long-sought goals of diagnostic imaging is precise tissue characterization. A clinician would like to scan a diagnostic region of an organ of the body and have the imaging system identify the characteristics of the tissue in the image. Ideally, the clinician would like the imaging system to identify a lesion as malignant or benign. While fully obtaining this objective remains yet to be accomplished, diagnostic imaging can nonetheless give the clinician clues as to the makeup of tissue. One technique in this area is elastography, which measures the elasticity or stiffness of tissues in the body. For example, breast tumors or masses with high stiffness might be malignant, whereas softer and more compliant masses are likely to be benign. Since the stiffness of a mass is known to correlate with malignancy or benignity, elastography provides the clinician with another piece of evidence to aid in diagnosis and determination of a treatment regimen.

Elastography as initially contemplated assessed tissue in the body when subjected to compressive pressure. When an ultrasound probe is pressed firmly against the body, underlying soft tissue will compress to a greater degree than underlying hard tissue. But elastography can be very operator-dependent, with results being influenced by where and how much pressure is being applied to the body. It would be desirable to be able to assess elasticity by a method which is not so operator-dependent.

An alternate approach to elasticity measurement is shearwave measurement. When a point on the body is compressed, then released, the underlying tissue is compressed downward, then rebounds back up when the compressive force is released. But since the tissue under the compressive force is continuously joined to surrounding tissue, the uncompressed tissue lateral of the force vector will respond to the up-and-down movement of the compressed tissue. A rippling effect in this lateral direction, referred to as a shearwave, is the response in the surrounding tissue to the downward compressive force. Furthermore, it has been determined that the force needed to push the tissue downward can be produced by the radiation pressure from an ultrasound pulse, and ultrasound reception can be used to sense and measure the tissue motion induced by the shear waves. Shearwave velocity is determined by local tissue mechanical properties. The shearwave will travel at one velocity through soft tissue, and at another, higher velocity through hard tissue. By measuring the velocity of the shear wave at a point in the body, information is obtained as to characteristics of the tissue such as its shear elasticity modulus, Young's modulus, and dynamic shear viscosity. The laterally propagating shearwave travels slowly, usually a few meters per second or less, making the shearwave susceptible to detection, although it attenuates rapidly over a few centimeters or less. See, for example, U.S. Pat. No. 5,606,971 (Sarvazyan) and U.S. Pat. No. 5,810,731 (Sarvazyan et al.) Since the same "push pulse" can be repeated for each measurement, the shearwave technique lends itself to objective quantification of tissue characteristics with ultrasound. Furthermore, the shear wave velocity is independent of the push pulse intensity, making the measurement less dependent upon the user.

The motion of tissue within the body caused by shearwave travel is very slight, however, usually on the order of tens of micrometers or less. Hence it is important that the location of shearwave generation, the focus of a push pulse, be chosen carefully so that a detectable shearwave is produced without unduly rapid attenuation. Some tissue structures within the body are known to adversely affect shearwave generation and propagation. One such structure is blood vessels. Shearwaves will not travel successfully through fluids, for example, a blood vessel. It is important, therefore, to avoid generating a shearwave where a blood vessel is located between the push pulse focal point and the target mass whose shearwave properties are to be measured. Another tissue structure which can adversely affect shearwave propagation is a region of significantly varying tissue stiffness between the push pulse focal point and the target mass. Such tissue can distort or weaken the shearwave, resulting in velocity measurement inaccuracy. Yet another problem for shearwave generation is motion due to breathing and other motional effects. A patient's breathing can produce movement in the target region, resulting in mislocation of the desired push pulse focus and the resultant shearwave with respect to the location of the target mass. Accordingly it is desirable to be able to detect these potential impediments to accurate shearwave generation in real time for each patient, so that accurately located shearwaves are generated without undue distortion or attenuation.

In accordance with the principles of the present invention, a diagnostic ultrasonic imaging system and method are described which automatically and adaptively identifies impediments to successful shearwave generation during a shearwave measurement exam and causes shearwaves to be generated at locations in the body which produce accurate tissue velocity measurement. Prior to shearwave generation one or more pilot images are acquired which identify underlying tissue distribution and motion characteristics. Such pilot images may be acquired as B mode images, colorflow images, tissue Doppler images and initial shearwave images. The pilot images are analyzed by a push pulse locator to determine when and where the most effective push pulses should be generated. Such pilot images are periodically reacquired so that locations for effective push pulses are periodically updated and refined. The pilot images may be displayed to a user or analyzed in the background, and the effects of the analysis and precise push pulse generation seen in the improvement of shearwave imaging and measurement.

In the drawings:

FIG. 2 illustrates the generation and tracking of a shearwave.

FIG. 2a illustrates the use of multiline tracking pulses to track the progression of a shearwave.

FIG. 3 illustrates an ultrasound image showing tissue distribution characteristics which are considered by a push pulse locator operating in accordance with the principles of the present invention.

Figure 1:
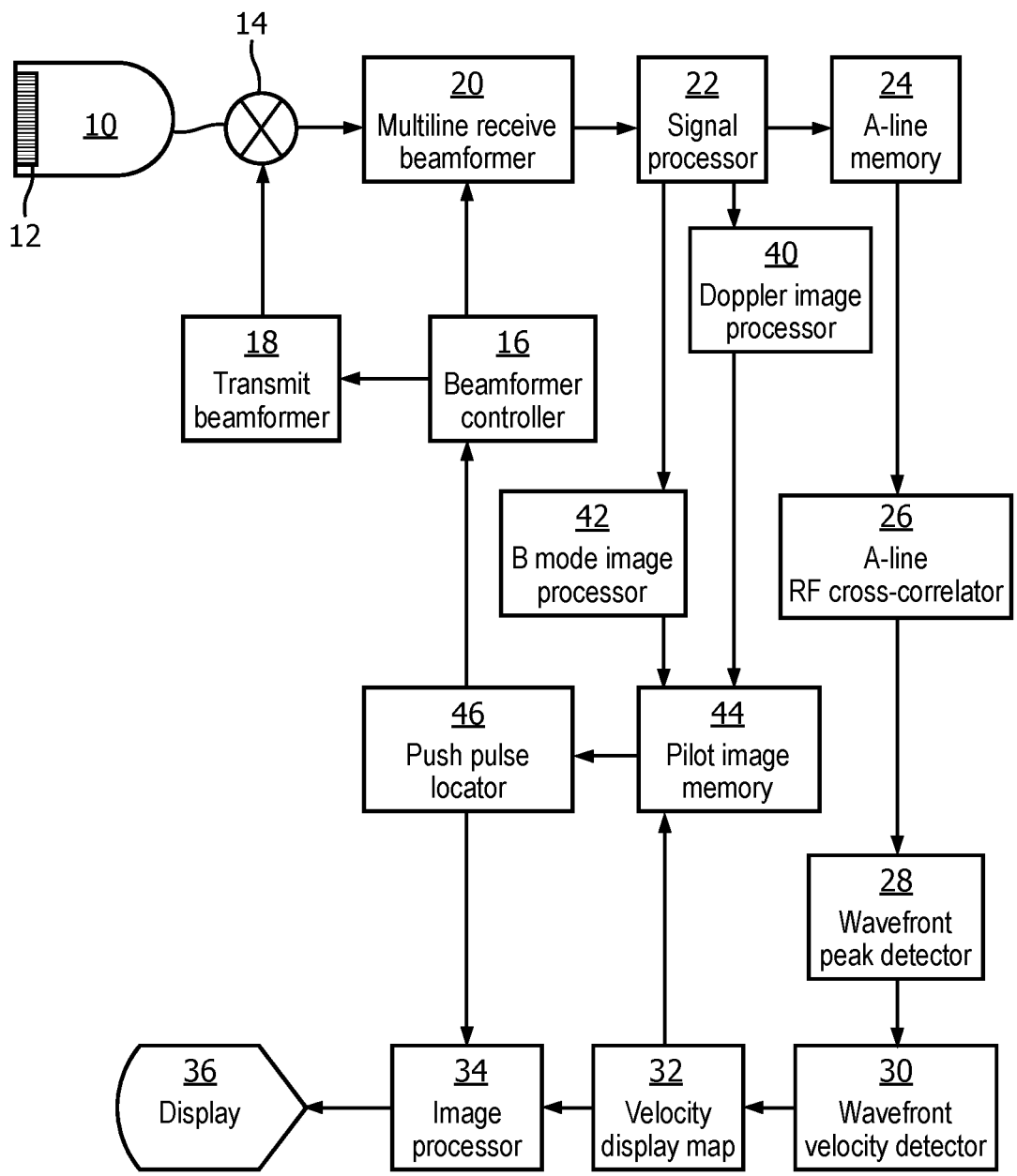
FIG. 1 illustrates in block diagram form an ultrasonic diagnostic imaging system constructed in accordance with the principles of the present invention.

Referring first to FIG. 1, an ultrasound system constructed in accordance with the principles of the present invention for the adaptive generation and measurement of shearwaves is shown in block diagram form. An ultrasound probe 10 has a transducer array 12 of transducer elements for transmitting and receiving ultrasound signals. The array can be a one dimensional or a two dimensional array of transducer elements. Either type of array can scan a 2D plane and the two dimensional array can be used to scan a volumetric region in front of the array. The array elements are coupled to a transmit beamformer 18 and a multiline receive beamformer 20 by a transmit/receive (T/R) switch 14. Coordination of transmission and reception by the beamformers is controlled by a beamformer controller 16. Measurement of shearwave velocity by an ultrasound system proceeds in two phases, a shearwave generation phase and a shearwave tracking phase. In the generation phase, a relatively high energy pulse (i.e., with a high mechanical index MI) called a push pulse is focused at a point in a subject, the focused energy causing physical movement of tissue. Thereafter during the tracking phase a shearwave emanates laterally outwards from the location of the push pulse, and is sampled and tracked by interrogation pulses called tracking pulses. The shearwave generation and tracking phases may be performed sequential or in parallel. During this tracking phase, the multiline receive beamformer of FIG. 1 produces multiple, spatially distinct receive lines (A-lines or tracking lines) of echo signals during a single transmit-receive interval as shown in FIG. 2a for the measurement of the travel of a shearwave. The echo signals are processed by filtering, noise reduction, and the like by a signal processor 22, then stored in an A-line memory 24. Temporally distinct A-line samples relating to the same spatial vector location are associated with each other in an ensemble of echoes relating to a common point in the image field. The r.f. echo signals of successive A-line sampling of the same spatial vector are cross-correlated by an A-line r.f. cross-correlator 26 to produce a sequence of samples of tissue displacement for each sampling point on the vector. Alternatively, the A-lines of a spatial vector can be Doppler processed to detect shear wave motion along the vector, or other phase-sensitive techniques can be employed. A wavefront peak detector 28 is responsive to detection of the shear wave displacement along the A-line vector to detect the peak of the shear wave displacement at each sampling point on the A-line. In a preferred embodiment this is done by curve-fitting, although cross-correlation and other interpolative techniques can also be employed if desired. The time at which the peak of the shear wave displacement occurs is noted in relation to the times of the same event at other A-line locations, all to a common time reference, and this information is coupled to a wavefront velocity detector 30 which differentially calculates the shear wave velocity from the peak displacement times on adjacent A-lines. This velocity information is coupled to a velocity display map 32 which indicates the velocity of the shear wave at spatially different points in a 2D or 3D image field. The velocity display map is coupled to an image processor 34 which processes the velocity map, preferably overlaying an anatomical ultrasound image of the tissue such as a B mode image with shading or colors representing tissue stiffness or elasticity, for display on an image display 36.

FIG. 2 illustrates the transmission of a focused high MI push pulse (e.g., MI of 1.9 or less so as to be within FDA diagnostic limits) along a single vector direction 84 to produce a shear wavefront. Pulses of high MI and long durations are used so that sufficient energy is transmitted to displace the tissue downward along the transmit vector and cause the development of a shearwave. The push pulse, which may also be the cumulative effect of a rapid sequence of such pulses, will displace the tissue at the focus downward, resulting in a shear wavefront 76, 66, 56, 46 emanating outwards from the displaced tissue. At the bottom of FIG. 2, wave 76 represents the shearwave shortly after push pulse generation. The lines above the bottom of the drawing illustrate the progressive travel of the shearwave 66, 56, and 46 at later points in time after shearwave generation.

As the shearwave travels outwards from the push pulse location, its motional effect on the surrounding tissue is sampled by tracking pulses 80. These tracking pulses are closely spaced and repetitively transmitted and echoes received to detect the effect of the shearwave travel before it attenuates. Shearwaves travel relatively slowly, generally at a velocity of one to ten meters per second. The sampling rate will be chosen in consideration of the frequency content of the shear wave displacement being detected so as to satisfy the Nyquist criterion for sampling. Since the purpose of the sampling is to sense and track the displacement effect of the shearwave as it progresses through the tissue, the vector locations may be located closer together for slowly moving shear waves and further apart for more rapidly moving shear waves. Other sequences of time-interleaving the vector sampling may also be employed. For reliable and rapid interrogation of a shearwave, multiline transmission and reception is preferably employed so that the transmission of a single tracking pulse can simultaneously sample a plurality of adjacent, tightly spaced, A-line locations. Referring to FIG. 2a, a preferred technique for multiline transmission and reception is shown. In FIG. 2a, a single A-line tracking pulse with a beam profile 82a, 82b is transmitted to insonify multiple receive line locations as indicated by the bracketed receive A-line locations 80. Preferably the tracking pulse is a so-called "fat pulse" as described in U.S. Pat. No. 4,644,795 (Augustine), for example. In this example four receive line locations 80 are insonified. Echoes from the four receive lines (4× multiline) are received in response to the single transmit pulse and are appropriately delayed and summed to produce coherent echo signals along each of the receive lines. Beamformers capable of producing such simultaneous multilines are described, for instance, in U.S. Pat. No. 5,318,033 (Savord), U.S. Pat. No. 5,345,426 (Lipschutz), U.S. Pat. No. 5,469,851 (Lipschutz), and U.S. Pat. No. 6,695,783 (Henderson et al.) These multiline beamformers are typically used to decrease the acquisition time and thereby increase the frame rate of live ultrasound images, which is particularly useful when imaging the beating heart and blood flow in real time echocardiography. They are also useful in 3D ultrasound imaging so that real time frame rates of display can be attained. See, in this regard, U.S. Pat. No. 6,494,838 (Cooley et al.) In an implementation of the present invention, the benefit of multiline acquisition is two-fold: it enables a closely-spaced sampling line density and rapid acquisition of a short duration shear wave which only travels a short distance through tissue before being dissipated by attenuation.

The ultrasound system of FIG. 1 also transmits pulses and receives echoes from the subject for the production of ultrasound images, referred to herein as pilot images, which are used to set the timing and location of push pulse generation in accordance with the present invention. During imaging, echoes received by the ultrasound probe 10 are beamformed, processed by signal processor 22, and coupled to one or both of B mode image processor 42 and Doppler image processor 40. As is known in the art, the B mode image processor produces images of tissue structure. The Doppler image processor produces various kinds of images of motion, including colorflow and power Doppler images of blood flow and tissue Doppler images of tissue motion. Tissue motion can also be spatially detected by correlating the image data of successive B mode images. A suitable correlation technique is the minimum sum of absolute differences (MSAD) technique as described in U.S. Pat. No. 9,107,564 (Burcher et al.) These processors are thus capable of producing several kinds of pilot images: flow images, motion (e.g., tissue Doppler or successive image correlation) images, and structural (B mode) images of the echogenicity of an image region. Another type of pilot image which is useful in an implementation of the present invention is an image of the relative stiffness or elasticity of tissue in an image region. There are several different types of such images. One is a strain image, an image of the response of tissue to stress, as described in U.S. Pat. No. 8,545,410 (Hope Simpson et al.) Another is an image of various parameters derived from shearwave measurement such as a spatial display of shear elasticity modulus, Young's modulus, and dynamic shear viscosity, which are all functionally related to shearwave velocity. These types of stiffness or elasticity images can be produced by overlaying a structural B mode image with colors or intensities representing a map of one of these functions as described above. Several of these types of pilot images, stiffness images, flow images, structural images, and motion images, are acquired and stored in pilot image memory 44.

In accordance with the principles of the present invention, one or more types of pilot images are analyzed by push pulse locator 46 to determine the location or timing of push pulse production for reliable shearwave generation. Preferably, both the location and timing of push pulse generation are determined by the push pulse locator. When the desired location and/or timing of generation of a push pulse is determined by the push pulse locator, this information is coupled to the beamformer controller 16 so that a push pulse is generated at the desired location by transmit beam-steering and focusing. The theory and operation of the push pulse locator 46 is described with reference to the remaining drawings of this patent.

Referring to FIG. 3, an ultrasound image 100 is shown which illustrates different problems that can arise which affect the choice of the location or timing of shearwave push pulse generation for optimal shearwave propagation. For illustrative purposes, the ultrasound image 100 contains information normally found in ultrasound images acquired by different modes of acquisition which are, in the context of the present invention, different pilot images. In the image of FIG. 3, a target mass 54 is seen which a clinician desires to assess by shearwave analysis. In a conventional ultrasound system, shearwaves might be generated from push pulses focused to the left of, to the right of, and from the center of the target mass 54, thereby producing shearwaves which travel through the target mass and their velocities are measured. But in the example of FIG. 3, there are obstacles to the successful generation of shearwaves from such push pulses. For instance, when a push pulse is generated to the left of target mass 54 at the circled "A", it will produce a shearwave which travels laterally to the right toward the target mass 54. But before reaching the target mass, the shearwave will traverse a region 58 which in this example is a region of higher stiffness (e.g., muscles, calcification, Coopers's ligament) than the surrounding tissue. Shearwaves traveling from the circled "A" at higher or lower positions may miss the higher stiffness region 58 and enter and pass through the target mass 54 at relatively different times from the time of shearwave production. Such stiffness irregularities can impact the strength of a generated shearwave and how far it will travel before it is too weak to detect. This can increase the difficulty of detected shearwave correlation and result in inaccuracy in shearwave velocity measurements. It would be preferable to locate a push pulse where the resulting shearwave only has to travel through tissue of homogeneous stiffness (e.g., normal tissue) before traveling through the target mass. In this example such a push pulse location is to the left of target mass 54 but to the right of different stiffness region 58.

But even with this optimization of the lateral placement of the location of push pulse generation, the desired measurement can still be affected by tissue motion. When measurements are being taken of shearwave velocity in abdominal organs such as the liver or spleen, the tissue may be moving with the breathing of the patient as the movement of the diaphragm alternately compresses and relaxes the abdomen. Breathing motion can cause the target mass 54 to move up and down in the image 100 as the patient inhales and exhales. This can cause push pulses generated a given depth from the transducer 12, such as the depth of the circled "C" in the image, to result in laterally produced shear waves which may alternately pass above, through, or below the target mass 54. Additionally, tissue motion during shearwave tracking phase can result in higher error in tracking shear waves thus created. An implementation of the present invention can detect the cycle of such breathing motion from tissue Doppler or other image motion data as shown below, and set a preferred time for the generation of a push pulse such as the moment when the push pulse location is aligned with the center of the target mass. A preferred time for push pulse generation, for instance, can be at the end of an exhale when the abdomen is momentarily stationary. The time during a breathing cycle can be displayed graphically to the user as by a histogram or graph so that the user can select the time of push pulse generation, or the system can select the time of generation when the push pulse location is at the best position with respect to the target mass.

FIG. 3 illustrates another problem which can affect push pulse and shearwave generation, which is a blood vessel in the path of the shearwave. The FIG. 3 image shows a blood vessel 52 in the vicinity of the target mass 54. When a push pulse is generated to the right of the target mass at the circled "B" location, the laterally traveling shearwave will encounter the blood vessel 52 before reaching the target mass 54. The blood of the vessel will sharply attenuate the shearwave, effectively blocking it from reaching the target mass. Thus, the push pulse locator 46 is adapted to recognize the presence of blood vessels and other fluid-filled structures such as bile ducts in a pilot image of flow, and set the focal point of a push pulse at a location where the path of shearwave travel to the target mass does not encounter flow. In the example of FIG. 3, the push pulse would be located, not at the location of the circled "B", but to the left of blood vessel 52.

It is seen that when a variety of different types of pilot images are acquired, the optimal locations and timing of push pulse generation can be determined which avoid a number of such problems. When a set of pilot images including a stiffness image, a flow image and a motion image are acquired and analyzed by the push pulse locator, for instance, push pulse locations and timing can be set which avoid all of the foregoing problems. The result of such analysis by the push pulse locator in the foregoing examples automatically generates push pulses in a lateral range indicated by lines 50, and in horizontal alignment with the target mass 54 as it moves with breathing motion. The resultant shearwave measurements are thus unaffected by these problems, which are adaptively avoided in real time for accurate diagnosis of the patient.

Figure 4:
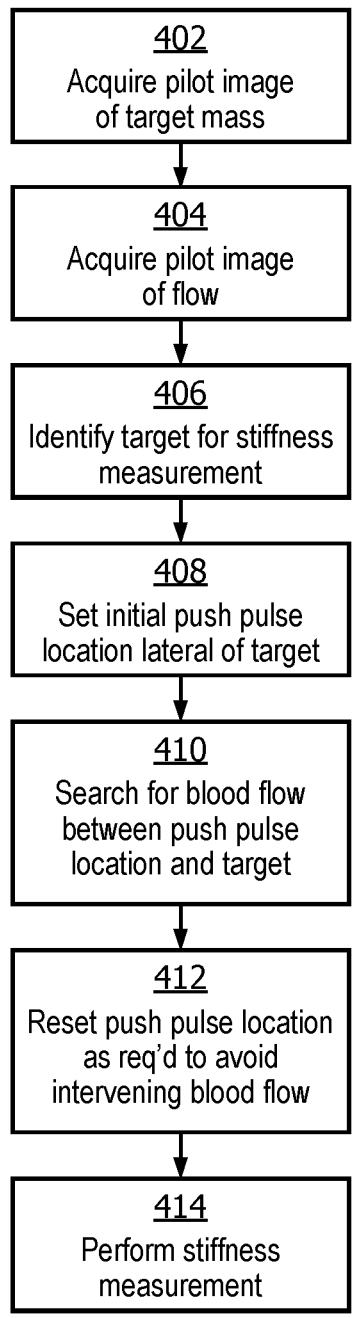
FIG. 4 is a flowchart illustrating the acquisition and use of a flow pilot image to set the location of a push pulse.

FIG. 4 is a flowchart which illustrates a method for operating the push pulse locator 46 to avoid problems posed by intervening vessels of flow between a location of push pulse generation and a target. In step 402, a pilot image of a target mass is acquired. This pilot image may be an initial shearwave stiffness image which at least approximately shows a region of different stiffness from normal tissue, or a B mode image where the echogenicity of a suspected lesion causes it to be distinguishable from surrounding normal tissue. In step 404 a pilot image of flow is acquired. This pilot image can be a colorflow image, a power Doppler image, or a B-flow image (B mode image showing flow), for example, or produced from correlation of temporally different B mode images. In step 406 the target for stiffness measurement by shearwave analysis is identified. This can be done manually by the user positioning a cursor over a target mass in an image, or automatically by the ultrasound system positioning a cursor over a target in a B mode or stiffness (e.g., strain or shearwave) image. When operating automatically, the system may display a message over or adjacent to a suspected target mass, asking the user in a displayed message "Target?" When the user confirms that the indicated target is the desired target, or moves the message with a mouse or trackball to a different location, the system will operate to measure to user-selected target. In step 408 the push pulse locator sets an initial push pulse location lateral of a target, such as to the right of, to the left of, or over a target mass in an image. In step 410 the push pulse locator analyzes the pilot flow image to search for the presence of any flow between the initial push pulse location and the target mass. If a region of flow in the shearwave path is found, the push pulse locator resets the push pulse location in step 412 to a location without intervening flow between the push pulse location and the target. If no flow is identified in the shearwave path, no reset of the push pulse location is necessary. When the appropriate adjustment (or no adjustment, when appropriate) of the push pulse location has been made, a push pulse is generated at the push pulse location and a stiffness measurement is made in step 414 using the resulting shearwave produced from that push pulse location.

Figure 5:
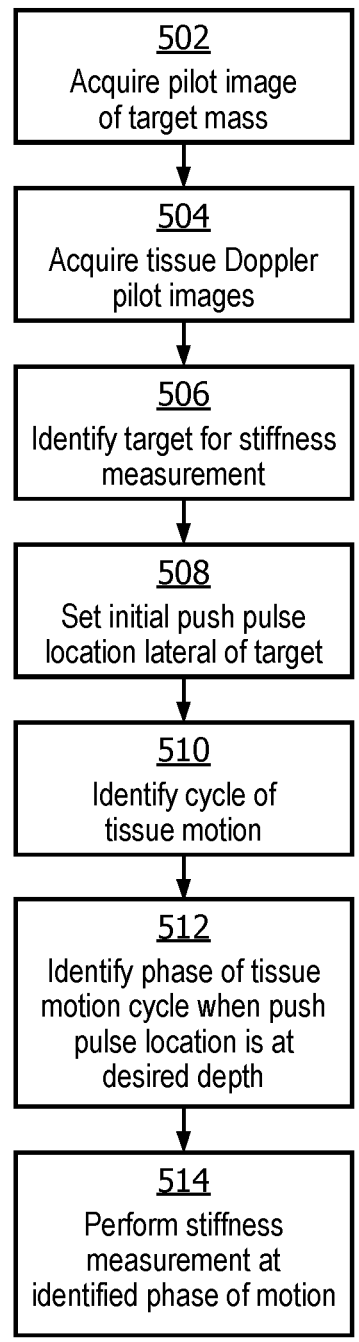
FIG. 5 is a flowchart illustrating the acquisition and use of tissue Doppler pilot images to set the timing of generation of a push pulse.

FIG. 5 illustrates a process for making a timing adjustment in the time of generation of a push pulse to account for tissue motion. In step 502 a pilot image of a target mass is acquired as described above. In step 504 a pilot tissue Doppler image or other image of tissue motion as described above is acquired. In step 506, a target mass for stiffness (shearwave) measurement is identified. In step 508 an initial location for push pulse generation is set. In step 508 the system sets an initial push pulse location lateral of a target, such as to the right of, to the left of, or over a target mass in an image. In step 510 the push pulse locator identifies a cycle of tissue motion from a sequence of images acquired during such a cycle. In step 512 the push pulse locator identifies a phase of the tissue motion cycle when a push pulse location is at a desired depth with respect to a target mass. This identification can be done automatically by the push pule locator from image analysis, or by manual indication by a user. In step 514 a shearwave stiffness measurement is performed by the system at the identified phase of tissue motion.

Figure 6:
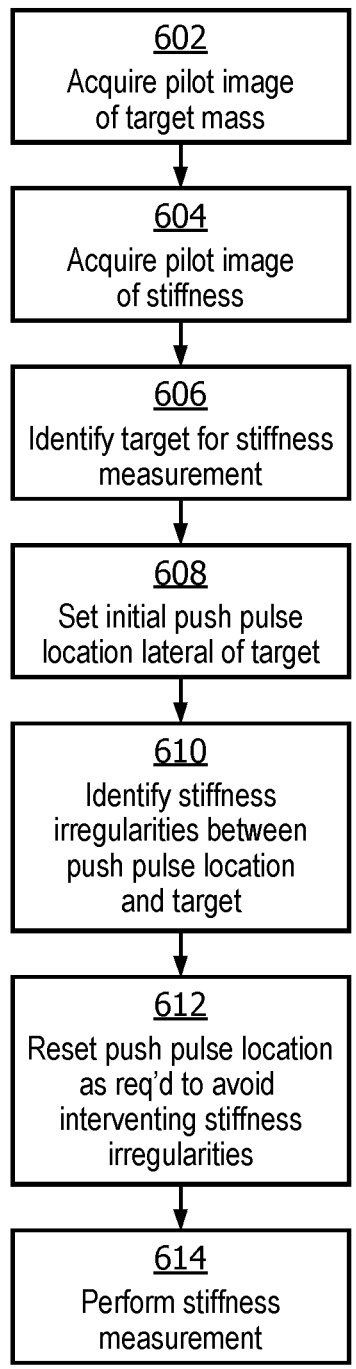
FIG. 6 is a flowchart illustrating the acquisition and use of a stiffness pilot image to set the location of a push pulse.

FIG. 6 illustrates a process for locating a push pulse focal point so that the resulting shearwave avoids identified stiffness inhomogeneities as it travels to the intended target mass. In step 602 the system acquires a pilot image of a target mass as described above. In step 604 the system acquires a pilot image of tissue stiffness, which can be a shearwave image or a strain image or a B mode image of tissue echogenicity as described above. In step 606, a target for stiffness measurement is identified which, as described above, can be done manually or automatically. In step 608 an initial push pulse location is set lateral of the target. In step 610 the push pulse locator analyzes the region of the pilot stiffness image for irregularities in stiffness between the push pulse location and the target. If any are found, the push pulse location is relocated so that only relatively homogeneous tissue is present between a push pulse location and the target. In step 614 a shearwave stiffness measurement is performed by the system by generating a push pulse at the relocated push pulse location, with the shearwave passing through relatively homogeneous tissue before encountering the target mass.

It can be seen that each of these different types of pilot images is useful for identifying and preventing a different kind of impediment to successful shearwave measurement. Thus, in a preferred implementation, a plurality of different types of pilot images are acquired so that all of these problems can be minimized or avoided. Pilot images are therefore acquired in sets of different types of images and all are used to search for and prevent these problems. It will be appreciated that such sets of pilot images can be acquired periodically and push pulse locations updated and adjusted continuously during shearwave measurements. When it is desired to acquire a full cycle of breathing or other periodic motion, it may take several seconds to acquire all of the needed motion pilot images to produce this information. A user may thus see the resultant shearwave measurements and images gradually improve and become more distinct as the push pulse locator continually improves the locations for push pulse generation. This process may be indicated to the user as by flashing a red indicator as pilot images are being acquired, then a green indicator as the push pulse locations are refined and optimized. This is done by the push pulse locator 46 commanding the beamformer controller 16 to steer and focus successive push pulses at constantly refined push pulse focal locations, and the shearwave image will improve correspondingly. Push pulses may then be generated to the left of, to the right of, and from the target mass so that a full set of measurements of velocity and stiffness characteristics are produced over the entire target region. An implementation of the present invention is useful for adaptive shearwave analysis and stiffness measurement of suspected tumors in the breast, prostate, thyroid, and musculoskeletal regions of the body.

Other implementation features will readily occur to those skilled in the art. For instance, many ultrasound systems are equipped with built-in tissue-specific setup parameters which are automatically invoked by selecting a specific type of diagnostic exam. Selection of a breast exam, for example, will not only set up the system for a breast exam, but this a priori information can also inform the push pulse locator that shearwave measurements will be performed in the breast so that the push pulse locator can look for and avoid locating push pulse focal points in less effective fatty breast tissue. Similarly, selection of a liver exam can inform the push pulse locator to look for bile ducts as well as blood vessels. Another useful feature is for the push pulse location(s) to be indicating graphically over an ultrasound image so that the user can spatially see the points from which shearwaves will be launched. A further feature is to enable the user to manually reposition the displayed push pulse locations if desired. Yet another useful feature is to mark on a displayed histogram or graph of breathing motion the time during the cycle at which shearwaves will be generated. A preferred implementation will turn off pilot image acquisition and analysis during a survey mode, when the user is moving the ultrasound probe to search for and obtain the best view of a suspected target mass. Once a preferred image of a target mass is obtained and the probe stops moving, the system can, automatically or at the command of the user, turn on pilot image acquisition and analysis for adaptive successful shearwave measurement and imaging. It will also be appreciated that the pilot images can be displayed to a user, or can be operated on by the push pulse locator in the background without displaying them to the user.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, for example, the Doppler image processor, the B mode image processor, and the push pulse locator, or components, processors, and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing images. The computer or processor may also include a memory. The memory devices such as the pilot image memory 44 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. A method for setting a focal point of a push pulse for shearwave generation comprising:
acquiring a plurality of pilot images of a target region including a target mass which is moving due to breathing motion, the pilot images containing tissue motion information of a cycle of the breathing motion;
analyzing the pilot images to determine a time of push pulse generation at the focal point in relation to the cycle of breathing motion which results in the generation of a push pulse at a moment during the breathing cycle when the push pulse focal point is aligned with the target mass so that a produced shear wave passes through the target mass; and
setting the time of generation of the push pulse in response to the analyzing.

2. The method of claim 1, wherein acquiring further comprises acquiring tissue Doppler pilot images.

3. The method of claim 1, wherein the steps of acquiring and analyzing are performed periodically with one or more newly acquired pilot images during a period of shearwave measurement.

4. The method of claim 1, wherein the step of analyzing pilot images further comprises determining a focal point location for the push pulse in one or more pilot images.

5. The method of claim 4, wherein the step of setting further comprises setting a focal point location for the generation of the push pulse in response to the analyzing.

6. The method of claim 1, wherein the step of analyzing further comprises identifying a cycle of tissue motion from a sequence of pilot images.

7. The method of claim 6, wherein the step of analyzing further comprises identifying a phase of the cycle of tissue motion for push pulse generation.

8. The method of claim 1, wherein setting the time of generation of the push pulse further comprises setting the time of generation of the push pulse to occur when a push pulse location is laterally aligned with the target mass.

9. The method of claim 1, wherein setting the time of generation of the push pulse further comprises setting the time of generation of the push pulse to occur at the end of an exhale of a breathing cycle.

\* \* \* \* \*